United States Patent
Wellman et al.

(10) Patent No.: US 7,314,479 B2
(45) Date of Patent: Jan. 1, 2008

(54) SPACE-CREATING RETRACTOR WITH VESSEL MANIPULATOR

(76) Inventors: Parris Wellman, 61 Taurus Dr., Apt. 3A, Hillsborough, NJ (US) 08844; Simon Cohn, 9 Webster St., Apt. 2, North Arlington, NJ (US) 07031; John Young, 48 Ashton Dr., Staten Island, NY (US) 10312; Thomas Swyst, 127 Highland Ave., Arlington, MA (US) 02476; James Pelletier, 601 Engamore La., Apt. T3, Norwood, MA (US) 02062; John Lapetina, 555 Duboce Ave., Apt. 12, San Francisco, CA (US) 94117; John P. Devlin, 241 Pringle St., Tewksbuy, MA (US) 01876

( * ) Notice: Subject to any disclaimer, the term of this patent is extended or adjusted under 35 U.S.C. 154(b) by 577 days.

(21) Appl. No.: 10/699,337

(22) Filed: Oct. 31, 2003

(65) Prior Publication Data

US 2005/0096677 A1 May 5, 2005

(51) Int. Cl.
*A61B 17/28* (2006.01)
*A61B 17/42* (2006.01)
*A61B 17/44* (2006.01)

(52) U.S. Cl. .................. 606/205; 606/206; 606/207
(58) Field of Classification Search ................ 606/201, 606/205, 206, 207
See application file for complete search history.

(56) References Cited

U.S. PATENT DOCUMENTS

| | | | |
|---|---|---|---|
| 2,002,594 A | 5/1935 | Wappler et al. | |
| 2,055,188 A | 9/1936 | Wappler et al. | |
| 3,799,150 A | 3/1974 | Bonnet | |
| 3,844,272 A | 10/1974 | Banko | |
| 4,052,980 A | 10/1977 | Grams et al. | |
| 4,391,282 A | 7/1983 | Ando et al. | |
| 4,573,451 A | 3/1986 | Bauman | |
| 4,605,009 A | 8/1986 | Pourcelot et al. | |
| 5,013,312 A | 5/1991 | Parins et al. | |
| 5,085,659 A | 2/1992 | Rydell | |
| 5,171,255 A | 12/1992 | Rydell | |

(Continued)

FOREIGN PATENT DOCUMENTS

EP 0 979 635 A2 2/2000

(Continued)

OTHER PUBLICATIONS

Guidant Instructions for Use: Short Port BTT, 2002.

(Continued)

*Primary Examiner*—Michael J. Hayes
*Assistant Examiner*—Michael Mendoza
(74) *Attorney, Agent, or Firm*—J. Gary Mohr

(57) ABSTRACT

An instrument for manipulating a vessel in a patient includes a cannula having a lumen for providing insufflation to create a working space in the tissue of a patient, and a first manipulator for manipulating a vessel located within the working space. The first manipulator is slidably movable within the cannula from a stowed position, where the first manipulator is substantially disposed within the cannula, to a forward position, where at least a portion of the first manipulator is disposed outside the cannula. The first manipulator is rotatable when in the forward position to an extended position.

6 Claims, 13 Drawing Sheets

U.S. PATENT DOCUMENTS

| | | |
|---|---|---|
| 5,324,289 A | 6/1994 | Eggers |
| D349,341 S | 8/1994 | Lichtman et al. |
| D350,606 S | 9/1994 | Koros et al. |
| 5,373,840 A | 12/1994 | Knighton |
| 5,403,312 A | 4/1995 | Yates et al. |
| 5,443,463 A | 8/1995 | Stern et al. |
| 5,445,638 A | 8/1995 | Rydell et al. |
| 5,458,598 A | 10/1995 | Feinberg et al. |
| 5,462,546 A | 10/1995 | Rydell |
| 8,456,684 | 10/1995 | Schmidt et al. |
| 5,484,436 A | 1/1996 | Eggers et al. |
| 5,512,037 A | 4/1996 | Russell et al. |
| 5,514,148 A | 5/1996 | Smith, III |
| 5,527,313 A | 6/1996 | Scott et al. |
| 5,531,744 A | 7/1996 | Nardella et al. |
| 5,536,234 A | 7/1996 | Niewman |
| 5,569,274 A | 10/1996 | Rapacki et al. |
| 5,573,534 A | 11/1996 | Stone |
| 5,573,535 A | 11/1996 | Viklund |
| 5,591,183 A | 1/1997 | Chin |
| 5,593,418 A | 1/1997 | Mollenauer |
| 5,601,581 A | 2/1997 | Fogarty et al. |
| 5,647,838 A | 7/1997 | Bloomer |
| 5,658,282 A | 8/1997 | Daw et al. |
| 5,665,085 A | 9/1997 | Nardella |
| 5,665,100 A | 9/1997 | Yoon |
| 5,667,480 A | 9/1997 | Knight et al. |
| 5,685,824 A | 11/1997 | Takei |
| 5,695,514 A | 12/1997 | Chin |
| 5,709,224 A | 1/1998 | Behl et al. |
| 5,709,680 A | 1/1998 | Yates et al. |
| 5,713,896 A | 2/1998 | Nardella |
| 5,722,934 A | 3/1998 | Knight et al. |
| 5,725,479 A | 3/1998 | Knight et al. |
| 5,730,748 A | 3/1998 | Fogarty et al. |
| 5,749,830 A | 5/1998 | Kaneko et al. |
| 5,759,150 A | 6/1998 | Konou et al. |
| 5,766,166 A | 6/1998 | Hooven |
| 5,772,576 A | 6/1998 | Knighton et al. |
| 5,776,128 A | 7/1998 | Eggers |
| 5,792,139 A | 8/1998 | Chambers et al. |
| 5,797,938 A | 8/1998 | Paraschac et al. |
| 5,797,941 A | 8/1998 | Schulet et al. |
| 5,797,947 A | 8/1998 | Mollenauer |
| 5,800,449 A | 9/1998 | Wales |
| 5,810,128 A | 9/1998 | Eriksson et al. |
| 5,810,808 A | 9/1998 | Eggers |
| 5,817,013 A | 10/1998 | Ginn et al. |
| 5,826,776 A | 10/1998 | Schulze et al. |
| 5,827,176 A | 10/1998 | Tanaka et al. |
| 5,827,279 A | 10/1998 | Hughett et al. |
| 5,833,690 A | 11/1998 | Yates et al. |
| 5,836,945 A | 11/1998 | Perkins |
| 5,846,185 A | 12/1998 | Carollo et al. |
| 5,853,417 A | 12/1998 | Fogarty et al. |
| RE36,043 E | 1/1999 | Knighton |
| 5,860,975 A | 1/1999 | Goble et al. |
| 5,865,726 A | 2/1999 | Katsurada et al. |
| 5,873,889 A | 2/1999 | Chin |
| 5,876,413 A | 3/1999 | Fogarty et al. |
| 5,891,140 A | 4/1999 | Ginn et al. |
| 5,891,141 A | 4/1999 | Rydell |
| 5,895,353 A | 4/1999 | Lunsford et al. |
| 5,899,913 A | 5/1999 | Fogarty et al. |
| 5,902,315 A | 5/1999 | BuBois |
| 5,902,316 A | 5/1999 | Mollenauer |
| 5,913,818 A | 6/1999 | Co et al. |
| 5,913,866 A | 6/1999 | Ginn et al. |
| 5,916,233 A | 6/1999 | Chin |
| 5,921,916 A | 7/1999 | Aeikens et al. |
| 5,921,919 A | 7/1999 | Chin et al. |
| 5,921,984 A | 7/1999 | Sutcu et al. |
| 5,922,001 A | 7/1999 | Yoon |
| 5,922,004 A | 7/1999 | DuBois |
| 5,925,045 A | 7/1999 | Reimels et al. |
| 5,928,135 A | 7/1999 | Knight et al. |
| 5,928,138 A | 7/1999 | Knight et al. |
| 5,938,680 A | 8/1999 | Ginn |
| 5,951,549 A | 9/1999 | Richardson et al. |
| 5,954,720 A | 9/1999 | Wilson et al. |
| D415,146 S | 10/1999 | Hori |
| 5,968,065 A | 10/1999 | Chin |
| 5,968,066 A | 10/1999 | Fogarty et al. |
| 5,970,982 A | 10/1999 | Perkins |
| 5,972,010 A | 10/1999 | Taheri |
| 5,976,168 A | 11/1999 | Chin |
| 5,980,549 A | 11/1999 | Chin |
| 5,984,937 A | 11/1999 | Morse et al. |
| 5,993,384 A | 11/1999 | Lunsford et al. |
| 6,017,358 A * | 1/2000 | Yoon et al. ............... 606/205 |
| 6,019,720 A | 2/2000 | Bito |
| 6,019,771 A | 2/2000 | Bennett et al. |
| 6,022,313 A | 2/2000 | Ginn et al. |
| 6,024,741 A | 2/2000 | Wialliamson, IV et al. |
| 6,030,384 A | 2/2000 | Nezhat |
| 6,036,713 A | 3/2000 | Kieturakis |
| 6,036,714 A | 3/2000 | Chin |
| 6,039,733 A | 3/2000 | Buysse et al. |
| 6,042,538 A | 3/2000 | Puskas |
| 6,053,863 A | 4/2000 | Chin et al. |
| 6,056,746 A | 5/2000 | Goble et al. |
| 6,059,782 A | 5/2000 | Novak et al. |
| 6,059,802 A | 5/2000 | Ginn |
| 6,066,137 A | 5/2000 | Greep |
| 6,068,639 A | 5/2000 | Fogarty et al. |
| 6,071,232 A | 6/2000 | Knighton et al. |
| 6,080,102 A | 6/2000 | Konou et al. |
| 6,083,223 A | 7/2000 | Baker |
| 6,086,586 A | 7/2000 | Hooven |
| 6,110,170 A | 8/2000 | Taylor et al. |
| 6,113,395 A | 9/2000 | Hon |
| 6,113,598 A | 9/2000 | Baker |
| 6,120,433 A | 9/2000 | Mizano et al. |
| 6,120,434 A | 9/2000 | Kimura et al. |
| 6,126,658 A | 10/2000 | Baker |
| 6,129,661 A | 10/2000 | Iafrati et al. |
| 6,135,999 A | 10/2000 | Fanton et al. |
| 6,139,489 A | 10/2000 | Wampler et al. |
| 6,162,173 A | 12/2000 | Chin et al. |
| 6,162,220 A | 12/2000 | Nezhat |
| 6,206,823 B1 | 3/2001 | Kolata et al. |
| 6,228,024 B1 | 5/2001 | Co et al. |
| 6,277,137 B1 | 8/2001 | Chin |
| 6,306,082 B1 | 10/2001 | Takahashi et al. |
| 6,306,345 B1 | 10/2001 | Bronshtein et al. |
| 6,309,345 B1 | 10/2001 | Stelzer et al. |
| 6,334,860 B1 | 1/2002 | Dorn |
| 6,348,037 B1 | 2/2002 | Chin et al. |
| 6,391,028 B1 | 5/2002 | Fanton et al. |
| 6,464,702 B2 | 10/2002 | Schulze et al. |
| 6,527,771 B1 | 3/2003 | Weadock et al. |
| 6,592,482 B2 | 7/2003 | Serkh |
| 6,592,604 B2 | 7/2003 | Hess et al. |
| 6,616,661 B2 | 9/2003 | Wellman et al. |
| 6,623,482 B2 | 9/2003 | Pendekanti et al. |
| 2003/0032864 A1 | 2/2003 | Friesen |
| 2003/0065323 A1 | 4/2003 | Hess et al. |
| 2003/0065348 A1 | 4/2003 | Hess et al. |
| 2003/0065349 A1 | 4/2003 | Hess et al. |
| 2003/0065351 A1 | 4/2003 | Hess et al. |

| 2003/0130674 | A1 | 7/2003 | Kasahara et al. |

FOREIGN PATENT DOCUMENTS

| WO | WO 99/12487 | 3/1999 |
| WO | WO 99/66842 | 12/1999 |
| WO | WO 99/66850 | 12/1999 |
| WO | WO 00/15116 | 3/2000 |

OTHER PUBLICATIONS

Guidant Instructions for Use: VasoView[R] 5 Harvesting Cannula Single-Use, 2001.

* cited by examiner

SPACE-CREATING RETRACTOR WITH VESSEL MANIPULATOR

FIELD OF THE INVENTION

The present invention relates generally to surgical devices, and more particularly, to a surgical device for retracting tissue and manipulating a vessel.

BACKGROUND OF THE INVENTION

Endoscopic vessel harvesting (EVH), particularly of the greater saphenous vein in the leg and the radial artery in the arm, is a surgical procedure for obtaining a graft vessel for a coronary artery bypass graft (CABG) procedure. A physician's assistant (PA) typically performs the EVH on one or both legs and/or arms of the patient by operating endoscopically with instruments actuated at a position remote from the operating site to harvest saphenous veins and/or radial arteries.

Because the vessels harvested during EVH are surrounded by tissue (of the arm or leg, for example), it is necessary to create an operative space so that the PA can dissect the vessel from the surrounding tissue. Operative space may be created by using insufflation, as is disclosed in U.S. Pat. No. 5,468,248, or by using mechanical retraction, as is disclosed in U.S. Pat. No. 5,902,315 or 6,592,604, the disclosures of which are hereby incorporated by reference. The insufflation method creates operative space by separating layers of tissue and then introducing a gas into the space between the layers to maintain the separation, whereas the mechanical retraction method simply uses a structure to hold the tissue layers apart.

Whether insufflation or mechanical retraction is used, the operator needs to manipulate the vessel to protect the vessel during the procedure by repositioning it within the operating field. For example, the vessel can be shielded by moving it away from a side branch when the side branch is transected. In this way, the vessel is protected from any injury that might be caused during that procedure.

One example of a device that provides for vessel manipulation is disclosed in U.S. Pat. No. 5,993,384. This device uses a "cradle" attached to a cannula that is movable from a first position when it is substantially housed within the cannula to a second position where it extends distally from the cannula. The wires to which the cradle is attached are bent such that when the cradle is extended, the cradle pushes the vessel away from the cannula. This solution may be non-optimal because the cradle has a limited number of available motions that make it more difficult to precisely position the vessel.

Another system for manipulating the vessel is disclosed in U.S. Pat. No. 5,902,315. In this case, a separate instrument (such as the Ethicon Endo-surgery vessel dissector) is inserted into the operative space to manipulate the vessel. While this approach allows for greater vessel manipulation, it has the disadvantage of requiring that the user must operate another instrument in the operating field.

SUMMARY OF THE INVENTION

Therefore it is an object of the present invention to provide instruments and methods for their use that overcome the disadvantages of conventional instrumentation known in the art.

The instrument according to the present invention is a tissue retractor that incorporates fine vessel manipulation elements that can be used to move the vessel within the operative space. This instrument can be operated using one hand by actuating finger-operated controls on the device handle.

In a preferred embodiment, visualization is provided through an endoscope that is detachably connected to the retractor or used in conjunction with the retractor or by other visualization means separate from the retractor. It is also possible to incorporate the endoscope within the tissue retractor.

One embodiment of the invention provides an instrument for manipulating a vessel in a patient that includes a working head shaped to define a working space in the tissue of a patient, and a first manipulator for manipulating a vessel located proximate the working space. The first manipulator has a retracted position and an extended position, and is disposed at least partially within the working space when in the retracted position.

Another embodiment of the invention provides an instrument for manipulating a vessel in a patient that includes a working head shaped to define a working space in the tissue of a patient and a first manipulator disposed within the working space and having at least a first portion and a second portion. The first and second portion are connected by an intermediate portion. The instrument also includes a second manipulator disposed within the working space that has a mating portion configured to be disposed between the first and second portion of the first manipulator when the first and second manipulators are in the stowed position.

Also provided is a method for creating operative space and manipulating a vessel with the instruments of the present invention. The method includes providing a retractor having at least a distal end shaped to define a working space in the tissue of a patient, and a first manipulator having a retracted position and an extended position. The first manipulator is disposed at least partially within the working space when the manipulator is in the retracted position. The method also includes making an incision in a patient, inserting at least the distal end of the retractor into the incision, creating a working space in the tissue of the patient near the vessel with the distal end of the retractor, and manipulating the vessel by moving the first manipulator from the stowed position to the extended position.

Also provided is a method of creating operative space and manipulating a vessel, including the steps of: (1) providing a retractor that defines a working space in the tissue of a patient, and a first manipulator and a second manipulator, each of which are disposed at least partially within the working space, the first manipulator and the second manipulator each having a retracted position and an extended position; (2) making an incision in a patient; (3) inserting at least the distal end of the retractor into the incision; (4) creating a working space in the tissue of the patient near the vessel with the distal end of the retractor; and (5) manipulating the vessel by moving one of the first manipulator and the second manipulator from the stowed position to the extended position.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE INVENTION

Although this invention is applicable to treat numerous and various types of tissue, it has been found particularly useful in the environment of harvesting blood vessels. Therefore, without limiting the applicability of the invention to harvesting vessels such as the saphenous vein or radial artery, the invention will be described in such environment. Furthermore, the devices of the present invention are preferably configured as disposable devices, however, the devices can also be configured as semi-reusable or reusable without departing from the scope or spirit of the present invention.

Figure 1:
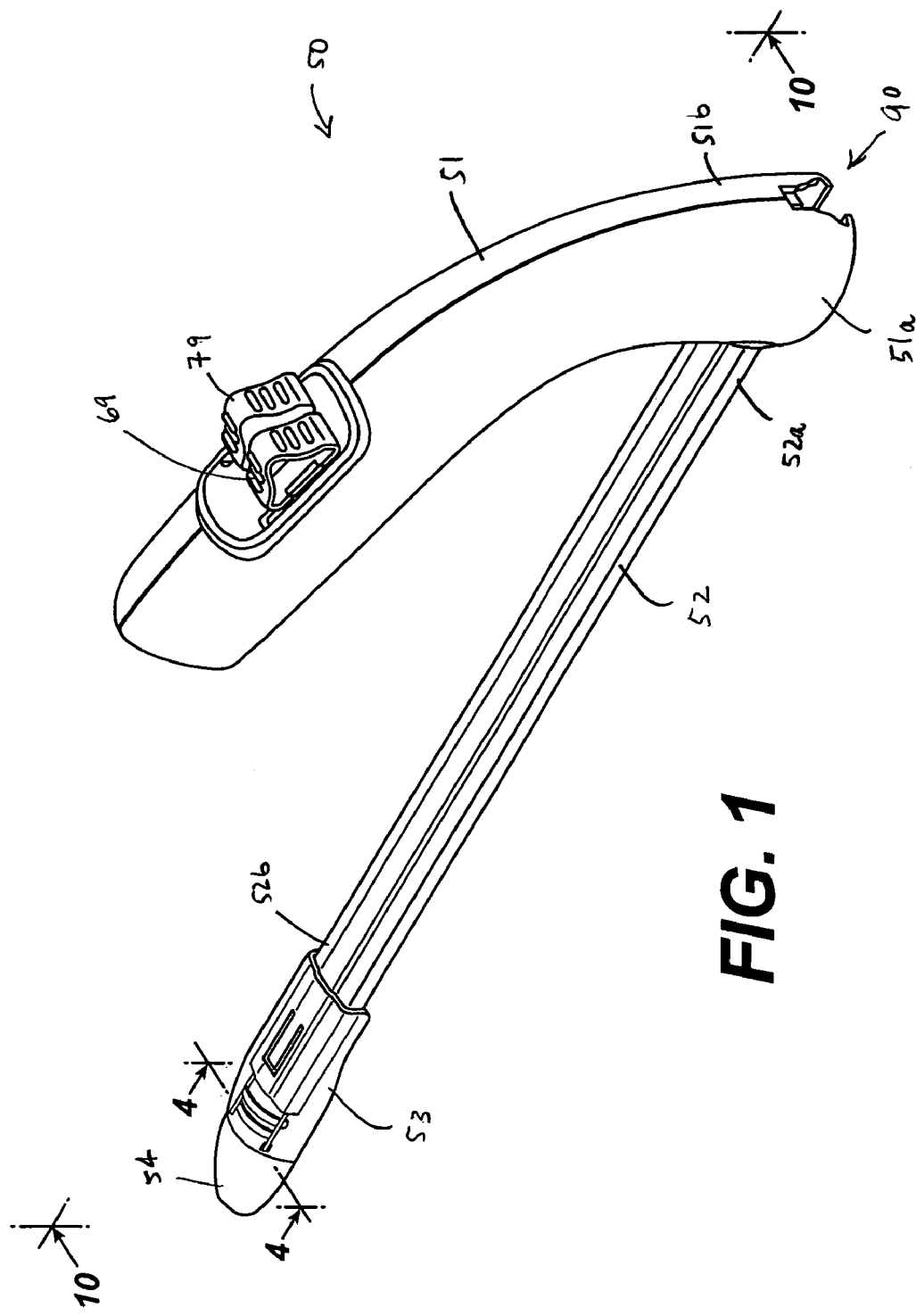
FIG. 1 is a perspective view of a preferred implementation of a retractor of the present invention.

Referring to FIG. 1, a retractor, generally referred to by reference number 50, is depicted. Retractor 50 includes a handle 51, also serving as, and alternatively referred to as a housing, a shaft 52 extending distally from handle 51, and a working head 53 attached to the distal end of shaft 52.

Retractor 50 is typically used with an endoscope attached to or inserted through handle 51 and beneath shaft 52 so that an operator may view into a working space created by working head 53. In a preferred embodiment, retractor 50 is used in conjunction with a multitool instrument more fully described in related U.S. patent application Ser. No. 10/699, 064, filed on the date of this application and assigned to Ethicon, Inc. U.S. Pat. No. 5,928,138 discloses how devices may be used with other instruments for dissecting and harvesting a vein, the disclosure of which is hereby incorporated by reference.

Figure 10:
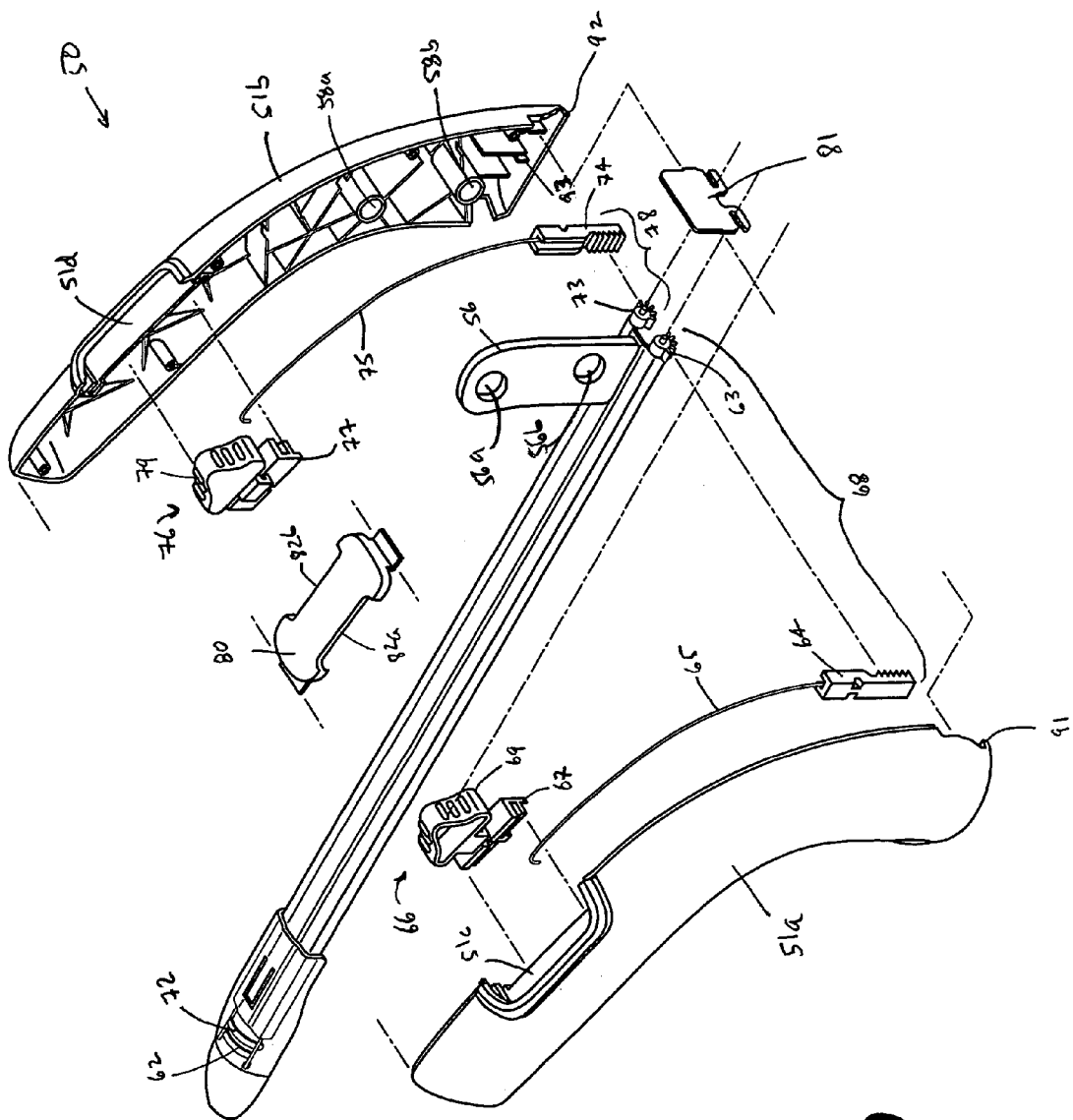
FIG. 10 is an exploded view of the retractor shown in FIG. 1.

Specifically, retractor 50 may include a docking port 90 that releasably mates with a dock 140 of a multitool instrument such that retractor 50 and the multitool instrument can be used together. Docking port 90 is preferably formed as part of handle 51. Referring to FIGS. 1 and 10, handle 51 is generally fabricated from a medical grade thermoplastic and is preferably formed in a "clamshell" design having first and second halves 51a, 51b. The clamshell design allows for easy assembly of the internal components. The halves 51a, 52b are fixed together by any means known in the art, such as by a press fit, or with a medical grade epoxy or adhesive, or by ultrasonic welding or by mechanical means, such as by screws, or by any combination of the above.

Figure 9:
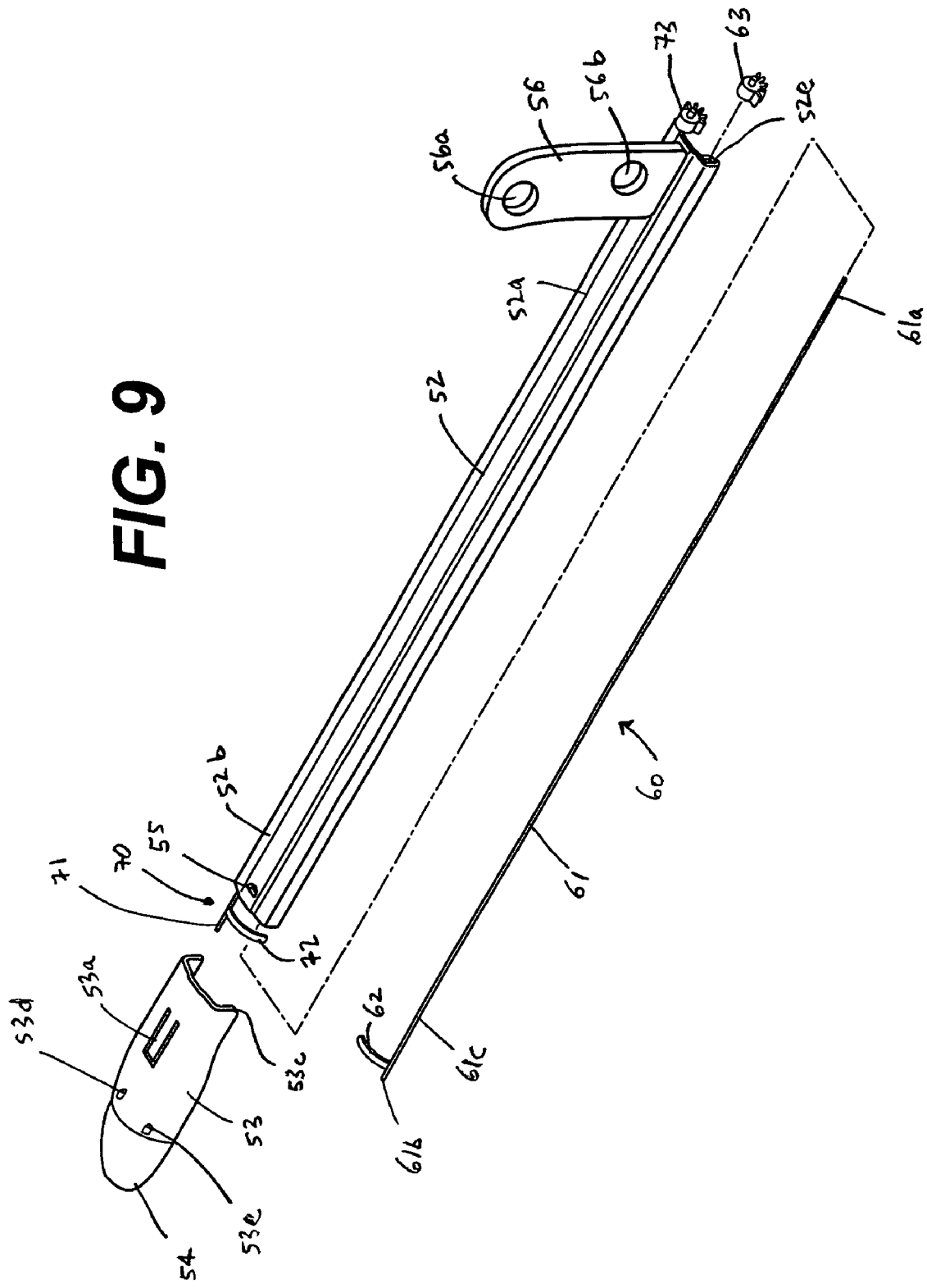
FIG. 9 is an exploded view of the retractor shown in FIG. 1 with the handle omitted for clarity.

Referring to FIGS. 1 and 9, shaft 52 is fabricated from a medical grade resilient material, such as stainless steel. A proximal end 52a of shaft 52 is attached to a member 56, which extends upwardly from proximal end 52a. Member 56 may have openings 56a, 56b to facilitate attachment to handle 51 by any means known in the art, such as a press fit or a medical grade epoxy or adhesive or heat-staking. Preferably, openings 56a and 56b of member 56 are sized to accommodate projections 58a, 58b (FIG. 10) that extend from each of halves 51a, 51b of handle 51 such that when halves 51a and 51b are brought together, the pairs of projections 57 and 58 capture member 56 by extending through openings 56a, 56b. A distal end 52b includes an opening 55 that is dimensioned to mate with a portion 53a of the working head 53. Opening 55 is preferably formed by removing material from a cross-sectional portion of the shaft 52. The removal of material to form opening 55 can be done by conventional machining or punching processes known in the art. Portion 53a of working head 53 is affixed to shaft 52 by any means known in the art, such as by a press fit and/or with a medical grade epoxy or adhesive. Shaft 52 is preferably shaped to form channels 52d and 52e (FIG. 3A) along a portion of the longitudinal length of shaft 52.

Figure 3:
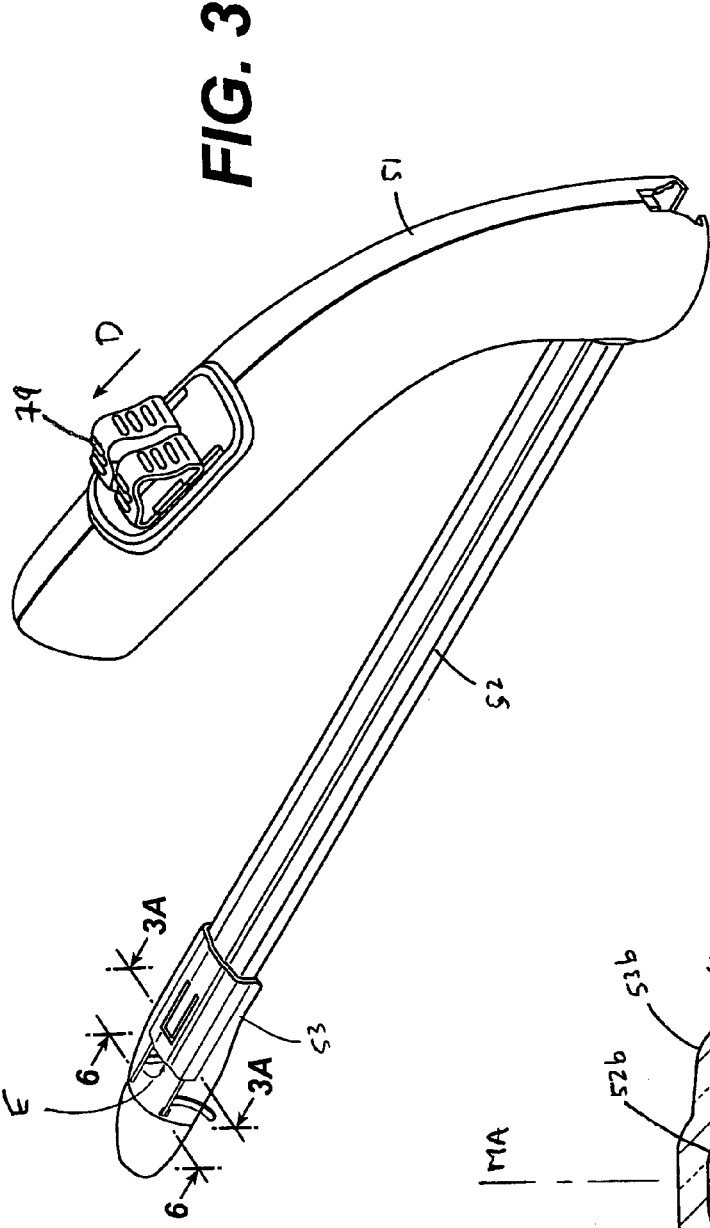
FIG. 3 is a perspective view of the retractor of FIG. 1, the retractor having a first and second paddle in an extended position.
Figure 3A:
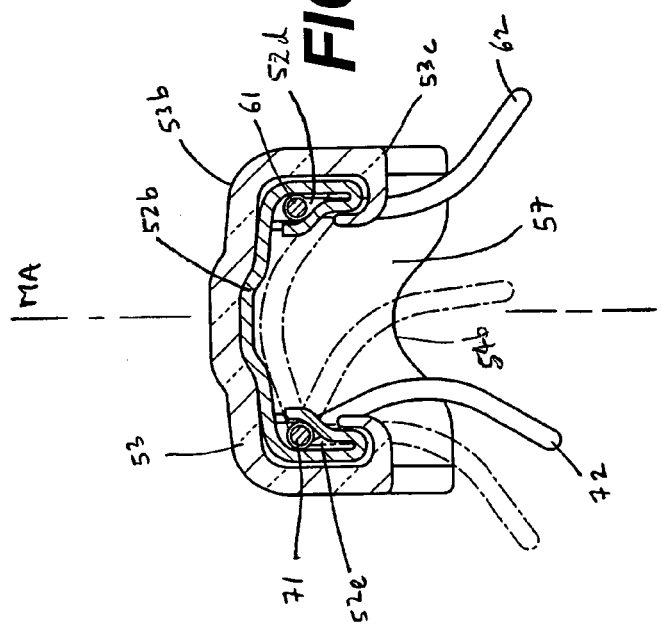
FIG. 3A is sectional view of the retractor shown in FIG. 3 taken along line 3A-3A.
Figure 7:
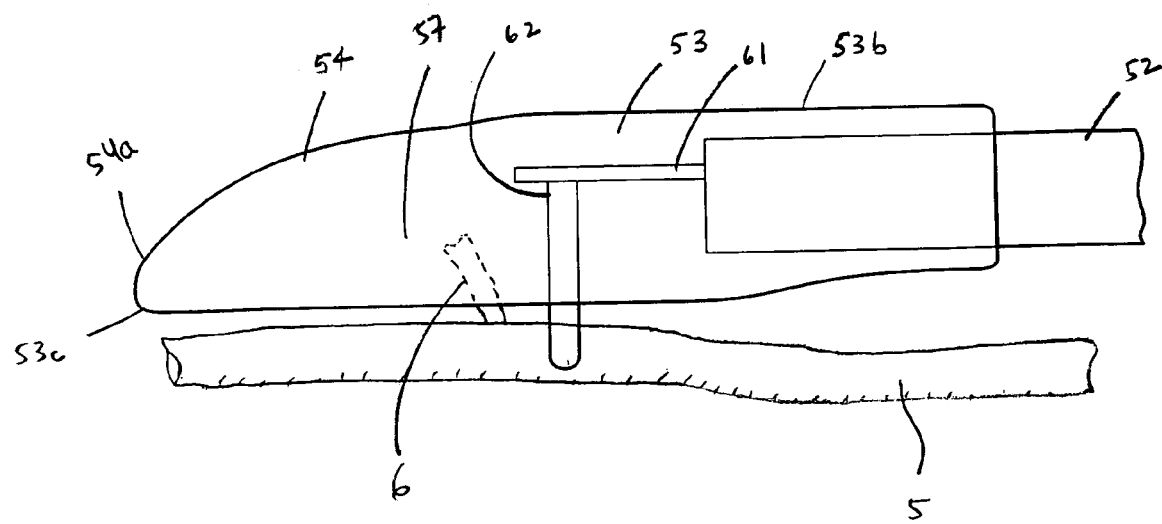
FIG. 7 is a side view of the retractor shown in FIG. 2.

Referring to FIGS. 7 and 9, working head 53 tapers to a distal end 54 having a leading edge 54a so that an operator can easily use working head 53 to separate tissue layers and isolate a vessel from surrounding tissues. As is shown in FIG. 3A, working head 53 may have a notch 54b in leading edge 54a to provide for better visualization and management of anterior side branches. Working head 53 includes an outer surface 53b that terminates at a peripheral edge 53c. Working space 57 is defined as the area between the tissue overlying the blood vessel and the tissue underlying the blood vessel separated by working head 53. Working head 53 also includes recesses 53d and 53e spaced apart laterally from one another and substantially aligned with channels 52d and 52e, respectively, of shaft 52.

Working head 53 is useful for grossly dissecting tissue away from a vessel, such as the saphenous vein, when introduced through an incision in tissue, and creating a working space to permit the separation of the vessel from the surrounding tissue during EVH. Working head 53 is preferably made of a medical grade, injection moldable plastic, such as polycarbonate, and is optionally clear for endoscopic viewing of tissue both inside and adjacent to working head 53. As is shown in FIG. 3A, working head 53 is preferably symmetrically shaped about a medial plane M and is generally concave. Working head 53 may have a spoon-shaped configuration, or it may consist of a bridge that extends for a portion or the full length of shaft 52, such as those depicted in U.S. Pat. No. 6,080,102, the disclosure of which is incorporate by reference. For example, working head 53 may consist of a tube having a semi-circular or a rhomboidal cross section when viewed axially. Such tubes may be entirely enclosed or have windows created therein. In short, working head 53 can be any shape that defines a working space 57 that facilitates the introduction of instruments into working space 57 in order to perform various steps of a surgical procedure.

Referring generally to FIG. 9, retractor 50 also includes a vessel retractor system for manipulating a vessel proximate working space 57 during EVH by repositioning the vessel within the operating field. In a preferred embodiment, the vessel retracting system includes a first manipulator 60, a first actuation system 68 (FIG. 10), a second manipulator 70 and a second actuation system 78. While the preferred system includes a first and second retractor, retractor 50 can include one or more retractors. In a preferred embodiment, retractor 50 includes a first manipulator 60 and a second manipulator 70, each disposed at least partially within working space 57. First manipulator 60 includes a first rod 61 having a proximal end 61a, a distal end 61b, a distal portion 61c, and a first paddle 62 extending from the distal portion 61c. First rod 61 is preferably made from stainless steel wire having a diameter approximately in the range of 0.025 inch to 0.075 inches, but most preferably 0.050 inches. A portion of rod 61 is disposed within channel 52d of shaft 52 with distal portion 61b extending beyond distal end 52b of shaft 52 and within working space 57. Distal end 61b is disposed within recess 53d of working head 53. Channel 52d and recess 53d are configured to retain a portion of rod 61, while permitting rod 61 to rotate freely within channel 52d and recess 53d. First paddle 62 is preferably attached to first rod 61 by laser welding, but could be attached by any means known to one skilled in the art.

Similarly, second manipulator 70 includes a second rod 71 having a proximal end 71a, a distal end 71b and a distal portion 71c, each of which are not shown in the figures, but are similar in form and function to the corresponding elements 61a, 61b and 61c of first manipulator 61. Manipulator 70 also includes a second paddle 72 extending from the distal portion 71c. Second rod 71 is preferably made from stainless steel wire having a diameter approximately in the range of 0.025 inch to 0.075 inches, but most preferably 0.050 inches. A portion of second rod 71 is disposed partially within channel 52e of shaft 52 with distal portion 71b extending beyond distal end 52b of shaft 52 and within working space 57. Distal end 71b is disposed within recess 53e of working head 53. Channel 52e and recess 53e are configured to retain a portion of second rod 71, while permitting second rod 71 to rotate freely within channel 52e and recess 53e. Second paddle 72 is attached to second rod 71 by laser welding, but could be attached by any means known to one skilled in the art.

Referring to FIG. 1, first paddle 62 and second paddle 72 are positioned offset distally from one another so as that one paddle does not to interfere with the other paddle's motion. Thus, first paddle 62 extends from first rod 61 at a location distal to the location where second paddle 72 extends from second rod 71. As such, first paddle 62 is retained within working head 53 at a location distal in a longitudinal direction to second paddle 72. Of course, either paddle could be configured in this way. In addition, first rod 61 and second rod 71 are offset from one another relative to the medial plane M of working head 53.

Figure 2:
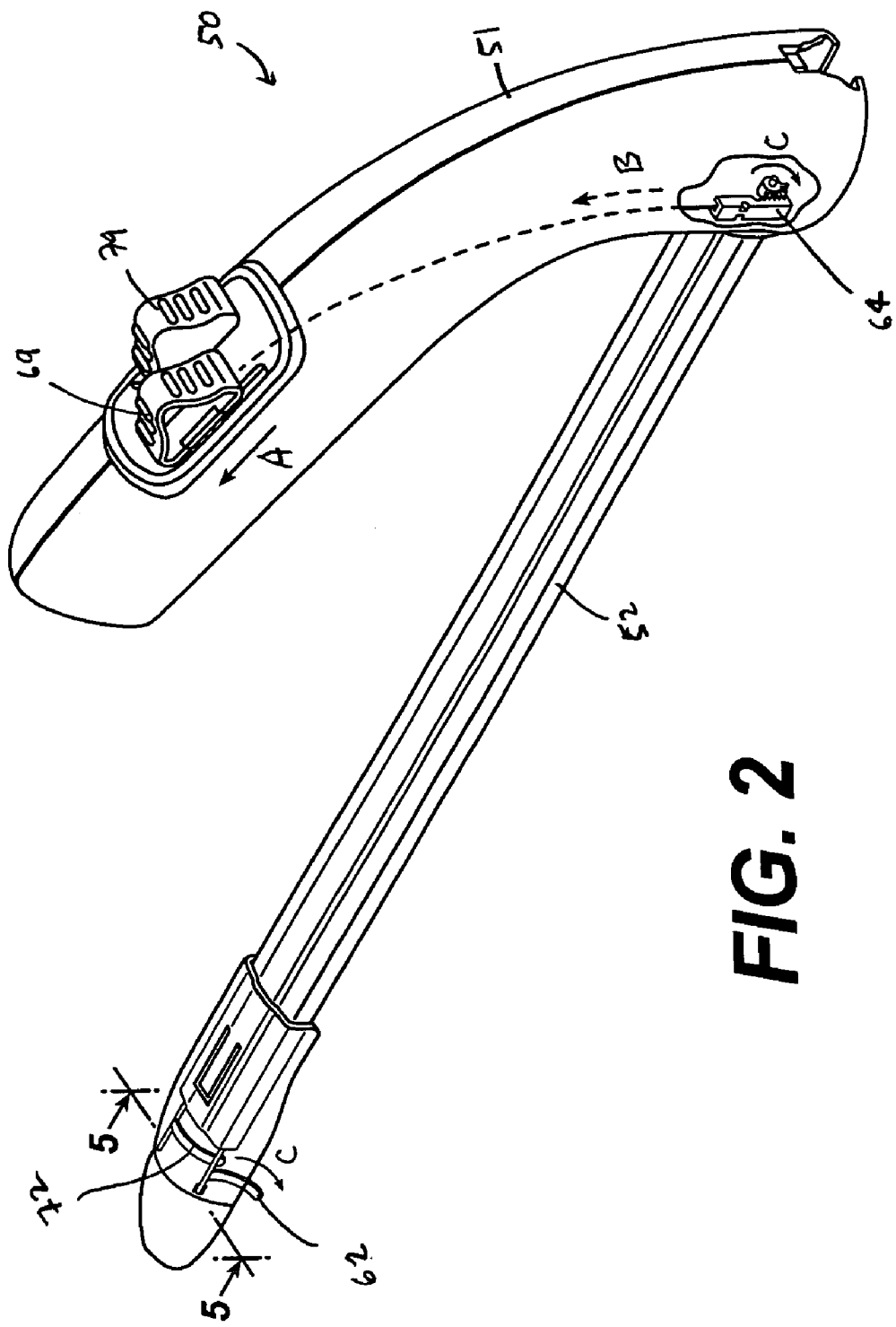
FIG. 2 is a perspective view of the retractor of FIG. 1, the retractor having a first paddle in an extended position.
Figure 8:
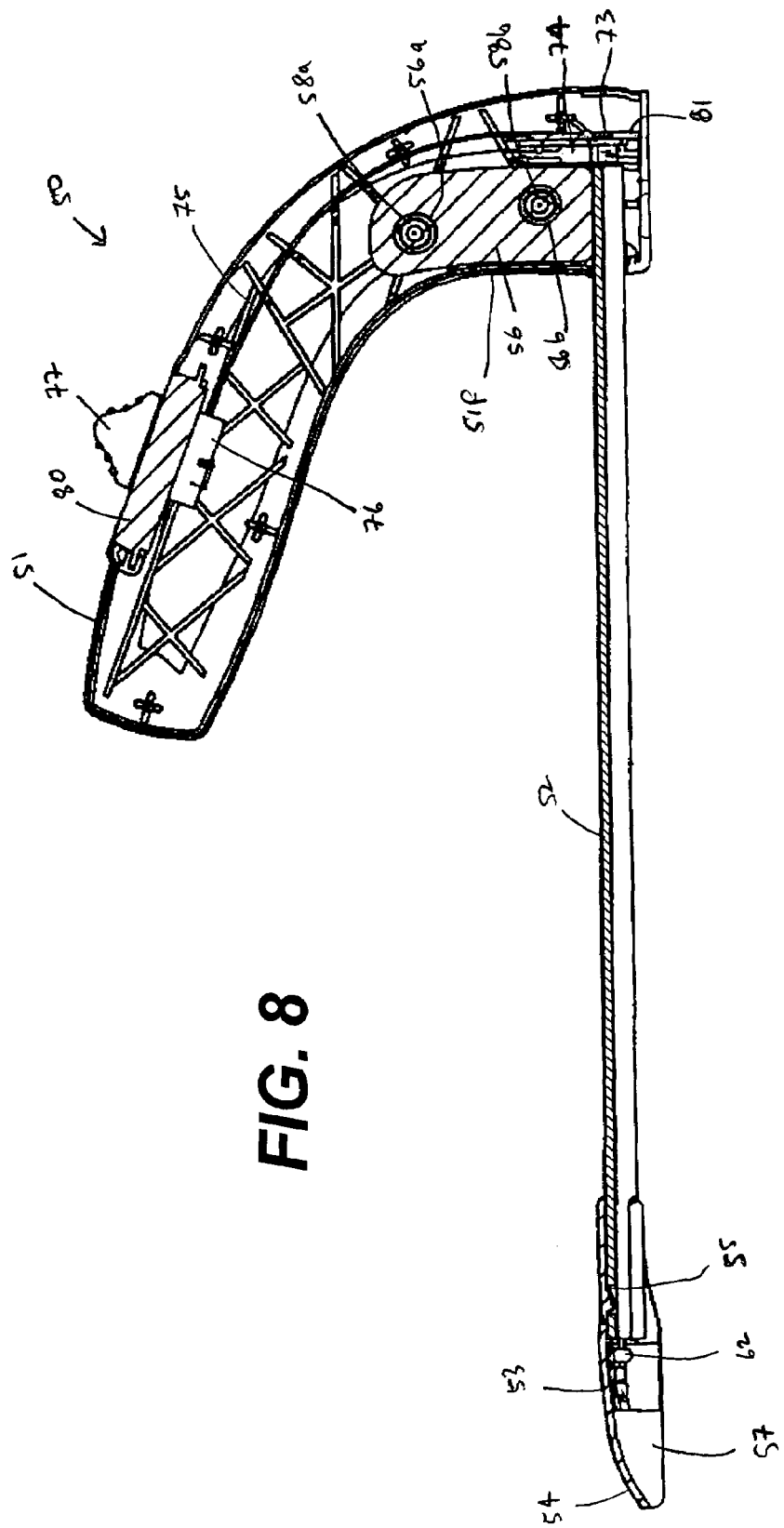
FIG. 8 is a side sectional view of the retractor shown in FIG. 1.

Referring now to FIGS. 2, 8 and 10, retractor 50 includes first actuation system 68 for moving paddle 62 between the retracted or stowed position and the extended position. In addition, the retractor 50 includes second actuation system 78 for moving paddle 72 between the retracted position and the extended position. The first actuation system is actuated by moving a first actuator 66 movably disposed in handle 52. First actuator 66 is preferably slidably disposed in handle 52 and operably connected to first paddle 62, such that moving first actuator 66 a predetermined distance rotates first paddle 62 between the retracted and extended positions. Similarly, the second actuation system is actuated by moving a second actuator 76 movably disposed in handle 52. Second actuator 76 is preferably slidably disposed in handle 52 and operably connected to second paddle 72, such that moving second actuator 76 a predetermined distance rotates second paddle 72 between the retracted and extended positions.

In a preferred embodiment, first actuator 66 of first actuation system 68 is operably attached to first paddle 62 so as to translate a linear motion to a rotational motion. First actuator 66 includes a first button 69 that the user moves to generate rotation of first paddle 62. First actuator 66 preferably also includes a slide 67 either integral with or separably attached to first button 69. First slide 67 is configured to retain one end of a wire 65 and to slidably ride in a slot 82a formed by lip 51c of handle 51 and a spacer 80. First wire 65 is connected at a distal end to first slide 67 and at a proximal end to a first rack 64. First rack 64, in turn is matingly engaged with a first pinion 63, which is preferably attached on one side to proximal end 61a of first rod 61 and rotates in a slot formed by backplate 81 and handle half 51a. Similarly, second actuator 76 of second actuation system 78 is operably attached to second paddle 72 so as to translate a linear motion to a rotational motion. Second actuator 76 includes a second button 79 that the user moves to generate rotation of second paddle 72. Second actuator 76 preferably also includes a slide 77 either integral with or separably attached to second button 79. Second slide 77 is configured to retain one end of a wire 75 and to slidably ride in a slot 82b formed by lip 51d of handle 51 and a spacer 80. Second wire 75 is connected at a distal end to second slide 77 and at a proximal end to a second rack 74. Second rack 74, in turn is matingly engaged with a second pinion 73, which is preferably attached on one side to proximal end 71a of second rod 71 and rotates in a slot formed by backplate 81 and handle half 51b.

Referring to FIG. 10, in a preferred embodiment, first and second racks 64, 74, first and second pinions 63, 73, and backplate 81 are all disposed within handle 51. Actuators 66, 76, racks 64, 74, pinions 63, 73 and spacer 80 are all preferably formed of a medical grade, injection moldable plastic, such as glass-filled nylon. Wires 65 and 75 are formed of a relatively flexible metal, such as stainless steel, and preferably range from 0.02 to 0.04 inches in diameter, and most preferably, is approximately 0.03 inches in diameter. Backplate 81 is preferably formed of stamped stainless steel.

Referring to FIG. 1, first button 69 and second button 79 are shown in their most proximal position, or the position closest to the operator's hand, within slots 82a and 82b. In this position, paddles 62 and 72 are retained within working head 53 in their stowed or retracted position. Referring to FIG. 2, displacement of first button 69 distally (or away from the operator's hand), in a direction depicted by arrow A, causes first wire 65 to move upwardly and distally (shown by broken arrow B), which in turn causes the first rack 64 to move upwardly. The motion of first rack 64 in turn causes first pinion 63 to rotate in the clockwise direction depicted as arrow C. As pinion 63 is attached to rod 61, rotation of first pinion 63 causes first paddle 62 to also rotate in the clockwise direction. Similarly, referring to FIG. 3, moving second button 79 distally in a direction depicted by arrow D causes second wire 75 to move upwardly and distally, which in turn causes second rack 74 to move upwardly, causing second pinion 73 and second paddle 72 to rotate in a counter-clockwise direction shown by arrow E.

First button 69 and second button 79 are positioned side by side such that a user that grasps retractor 50 with one hand, may actuate either or both buttons by using a thumb or finger. Thus, the user can manually retract tissue to form working space 57 and retract the vessel being harvested by using retractor 50, without the need for a separate instrument. Further, because retractor 50 includes first paddle 62 on one side of the medial line of retractor 50 and second paddle 72 on the other side of the medial line of retractor 50, the user may move the vessel to one side away from the medial line of retractor 50 using first paddle 62 or the other side away from the medial line of retractor 50 using second paddle 72, without the need to reposition or rotate retractor 50. Thus, in the event the user would like to transect a side branch on the right side of vessel, the user can use first paddle 62 to manipulate the vessel away from the side branch, and, similarly, where the user would like to transect a side branch on the left side of vessel, the user can use second paddle 72 to manipulate the vessel away from the side branch.

While the preferred embodiment depicts a first and second actuation system 68, 78, it is contemplated that first retractor and second retractor could be actuated using one actuation system. For example, rather than having two buttons that move within slots 51c, 51d, a single button can be toggled left or right to engage slide 67 or slide 77 depending upon which manipulator the user wanted to actuate. As a result, other than the toggle motion, the remainder of the actuation mechanism would work similarly to the described device; i.e., slides 67, 77 could move wires 65, 75 and racks 64, 74 to act upon pinions 63, 73 and manipulators 60, 70.

Figure 4:
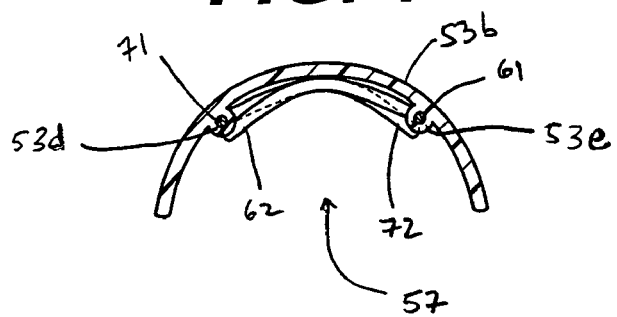
FIG. 4 is a sectional view of the retractor shown in FIG. 1 taken along line 4-4.
Figure 5:
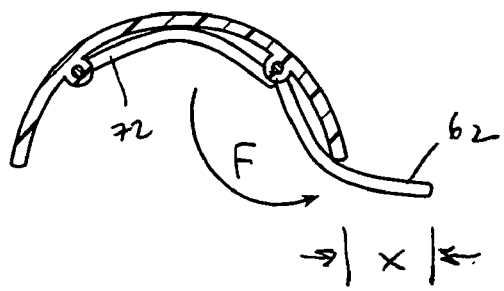
FIG. 5 is a sectional view of the retractor shown in FIG. 2 taken along line 5-5.
Figure 6:
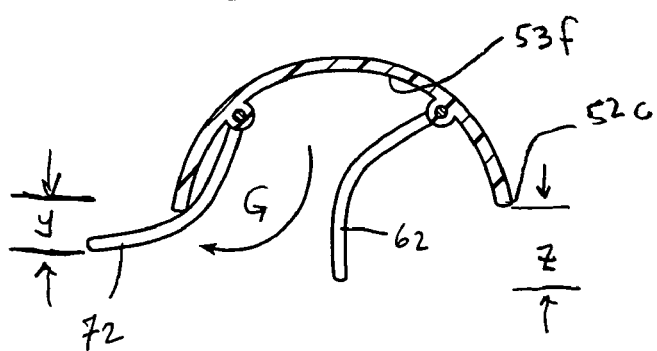
FIG. 6 is a sectional view of the retractor shown in FIG. 3 taken along line 6-6.

Referring to FIGS. 4-7, the details of the distal end of retractor 50 are shown. Referring to FIG. 4, first paddle 62 and second paddle 72 are shown in their stowed or retracted position. First paddle 62 and second paddle 72 are positioned to nest longitudinally in a side-by-side configuration close to a portion of the interior surface 53f of working head 53. In the stowed position, first paddle 62 and second paddle 72 are preferably shaped to substantially minimize the amount of working space obstructed by the paddles themselves. Preferably, as is shown in FIG. 5, first paddle 62 may rotate about the pivot point defined in recess 53d through an arc F of approximately 100 to 140 degrees, but most preferably 120 degrees. Similarly, as is shown in FIG. 6, second paddle 72 may rotate about the pivot point defined in recess 53e through an arc G of approximately 100 to 140 degrees, but most preferably 120 degrees. In each case, however, it is contemplated that the angle of rotation could be greater or smaller depending upon the location of recesses 53d, 53e and the curvature of working head 53.

As is shown in FIGS. 5 and 7, first paddle 62 extends below peripheral edge 53c when first paddle 62 is in the extended position. Preferably, first paddle 62 has a curved portion that forms a concave surface that faces away from working head 53 when in the extended position. In a preferred embodiment, when in the fully extended position, paddles 62 and 72 extend a distance X of approximately 0.10 inches to 0.25 inches medially outwardly (FIG. 5) from working head 53, but most preferably approximately 0.15 inches, and downwardly (FIG. 6) from working head 53 a distance Y of approximately 0.15 inches to 0.35 inches, but most preferably approximately 0.20 inches. When paddle 62 or 72 is extended below peripheral edge 53c normal to pivot point 53d, 53e, the tip of paddle 62, 72 (FIG. 6) preferably extends a distance Z of approximately 0.15 inches to 0.35 inches below edge 52c, but most preferably approximately 0.25 inches. The length of the paddles is preferably configured to be long enough to manipulate a vessel to a position that does not interfere with the working space, but short enough so as not to be prevented from rotating by the layer of tissue at the bottom of the working space when the paddles are actuated.

Figure 11:
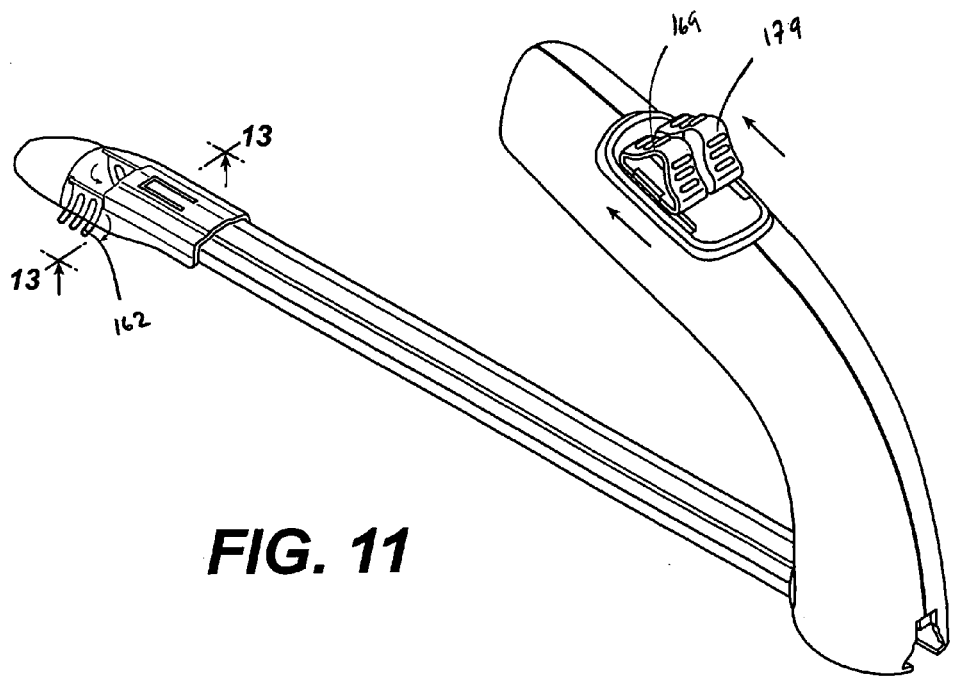
FIG. 11 is a perspective view of a first variation of the retractor of the present invention depicting wireform paddles.
Figure 12:
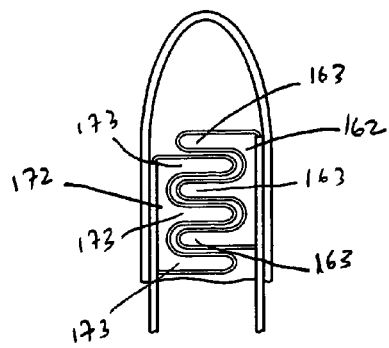
FIG. 12 is a bottom plan view of the retractor shown in FIG. 11 with the wireform paddles in the stowed position.
Figure 13:
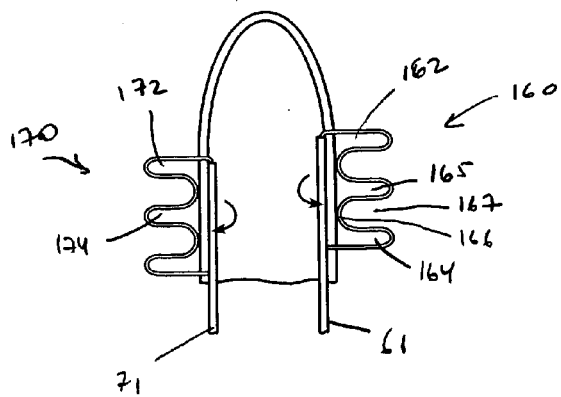
FIG. 13 is a bottom plan view of the retractor shown in FIG. 11 with the wireform paddles in the extended position.

FIGS. 11-13 show a second variation of first and second manipulators of the present invention, depicted as first manipulator 160 and second manipulator 170. FIG. 11 is a perspective view and FIGS. 12 and 13 are bottom plan views showing first manipulator 160 that includes a first mating paddle 162 fixed to rod 61, and second manipulator 170 that includes a second mating paddle 172 fixed to rod 71. Referring to FIG. 12, mating paddle 162 preferably includes fingers 163, configured to mate or interlace with fingers 173 of mating paddle 172 when in the stowed position. Mating paddles 162, 172 may be formed of wire as shown in the figures or may be a solid material, such as plastic or stainless steel. Mating paddles 162, 172 are shown as having three fingers 163, 173, but the paddles may have two or more fingers that mate with one another when in the stowed position. Further, the shape of the fingers may differ considerably from what is shown, so long as the first paddle has at least two portions connected by an intermediate portion such that a space between the at least two portions mates with a portion of the second paddle. For example, referring to FIG. 13, first paddle 162 includes a first portion 164 and a second portion 165 connected by an intermediate portion 166 such that a space 167 is created between first and second portions 165 and 166. Second paddle 172 includes at least one portion 174 configured to mate with first paddle 162 such that portion 174 occupies space 167 when paddles 162, 172 are in the stowed position. As is shown in FIG. 11, the paddles 162 and 172 may be actuated similarly to paddles 62 and 72 of the first embodiment, by moving buttons 169, 179 distally to rotate paddle 162 and 172, respectively.

Method of Use

FIG. 7 is a side view of retractor 50 being used in a surgical procedure in combination with a multitool instrument (not shown) for endoscopically harvesting a vessel 5 for use in a coronary artery bypass graft (CABG) surgical procedure. The multitool instrument and its method of use are disclosed in co-pending U.S. patent application Ser. No. 10/699,063, filed on even date herewith, and are hereby incorporated by reference.

Multitool instrument comprises a cannula having a dock disposed thereon, which may be inserted into docking port 90 of retractor 50. Multitool instrument also includes an endoscope for visualizing the tissues within working space 57. To utilize the instruments, a physician or physician's assistant determines the location of a vessel to be dissected, and makes an incision in the patient. The user then inserts retractor 50 into the incision and bluntly dissects the tissue surrounding vessel using working head 53. If the intention is to extract vessel 5, it is preferable to dissect as much tissue from around the vessel as possible. The user manipulates retractor 50 to advance working head 53 along vessel 5, separating tissue from vessel 5 and providing a working space for accessing and visualizing vessel 5 and a plurality of side branches, one of which is shown as reference numeral 6.

The user then uses multitool instrument to free vessel 5 from the surrounding tissue and isolate side branches of the vein that must be ligated prior to removal of vessel 5 from the patient's leg. As noted above, multitool instrument may be located above vessel 5, when docked with retractor 50, or may be positioned below shaft 52 of retractor 50 in an undocked configuration.

Referring to FIG. 7, the user manipulates either paddle 62 and/or 72 of retractor 50 to position vessel 5 away from the multitool instrument permitting the user to dissect, clamp, coagulate, and cut tissue within working space 57. In particular, when side branches 6 are encountered, the user can manipulate vessel 5 using, for example paddle 62 of retractor 50 such that vessel 5 is protected. In this manner, side branches 6 are isolated and exposed and a surgical tool introduced via the multitool instrument (or through cannula 252) can cauterize and cut side branch 6 without damaging vessel 5. The harvesting procedure continues in this manner until the vessel is hemostatically isolated from the surrounding tissues and blood supply along the portion to be harvested. Once the user completes the dissection and vessel 5 is freed of its surrounding tissue, retractor 50 can be withdrawn through the incision. Vessel 5 can then be removed from its native location and prepared for use in a coronary bypass procedure, for example.

It should be understood that paddles 62, 72 can operate in tandem or can be manipulated such that they work independently of one another. For example, paddle 62 can be extended independently of paddle 72 as it is positioned distally to paddle 72. Paddle 72 may also bypass paddle 62 by first extending each paddle to a position forward of the distal end of cannula 52, rotating paddle 72 such that it does not interfere with paddle 62, and then retracting paddle 62 into the stowed position within cannula 52.

Retractor 50 is especially suited for vessel harvesting, but are not limited to this surgical procedure. Retractor 50 may be used to retract many different types of tissue, and, similarly, multitool instrument 100 may be used to dissect, clamp, coagulate, and cut tissues during other types of endoscopic and open surgical procedures. For example, the instruments can also be used to remove other discrete tissues, such as tumors, to ligate fallopian tubes for fertility control, to ligate and transect bile ducts for nephrectomy, or to transect ligaments or other tissue structures.

Second Embodiment

Figure 14:
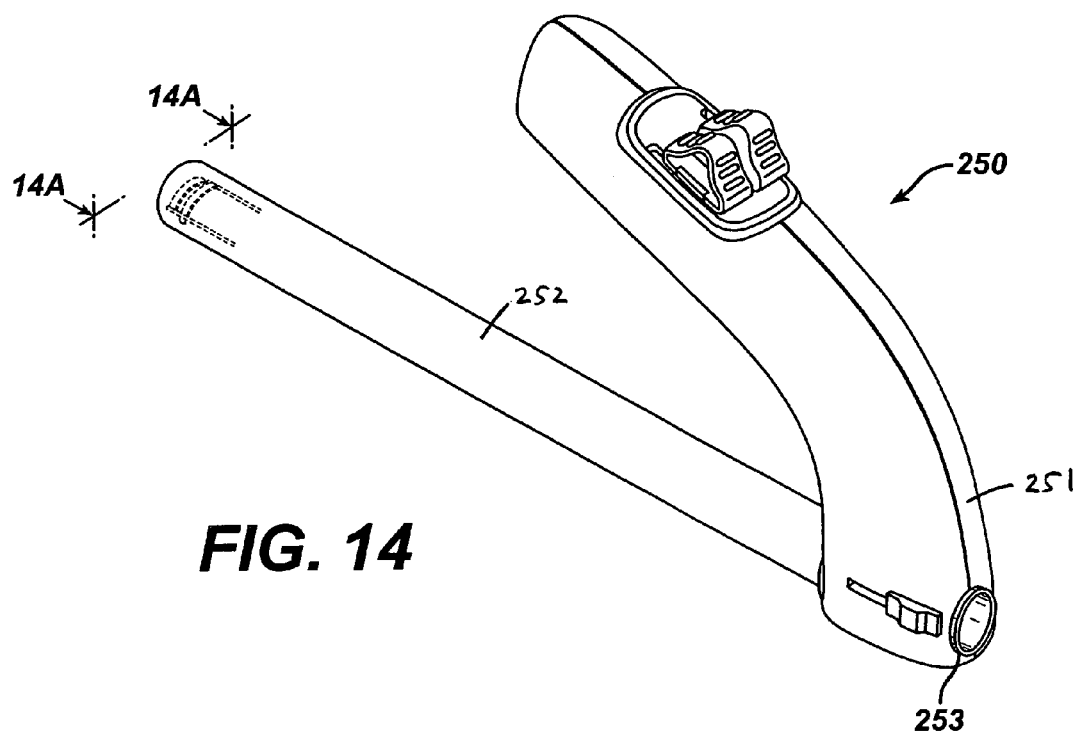
FIG. 14 is a perspective view of a second variation of the retractor of the present invention with the paddles in the stowed position.

Referring to FIGS. 14-20, a second embodiment of the invention is depicted. In this embodiment, the manipulation system is housed in a cannula that creates working space via insufflation rather than by using mechanical retraction as with the first embodiment. FIG. 14 depicts an instrument 250 that includes a cannula 252 and a handle 251 extending from the proximal end of cannula 252. Handle 251 has a throughhole 253 that permits communication with an insufflation source (not shown) and also permits an endoscope and other instruments (not shown) to be passed therethrough. Instrument 250 of the present invention provides benefits when dissecting vessels from tissue in a patient, however, such a use is given by way of example only and does not limit the scope or spirit of the present invention.

Figure 17:
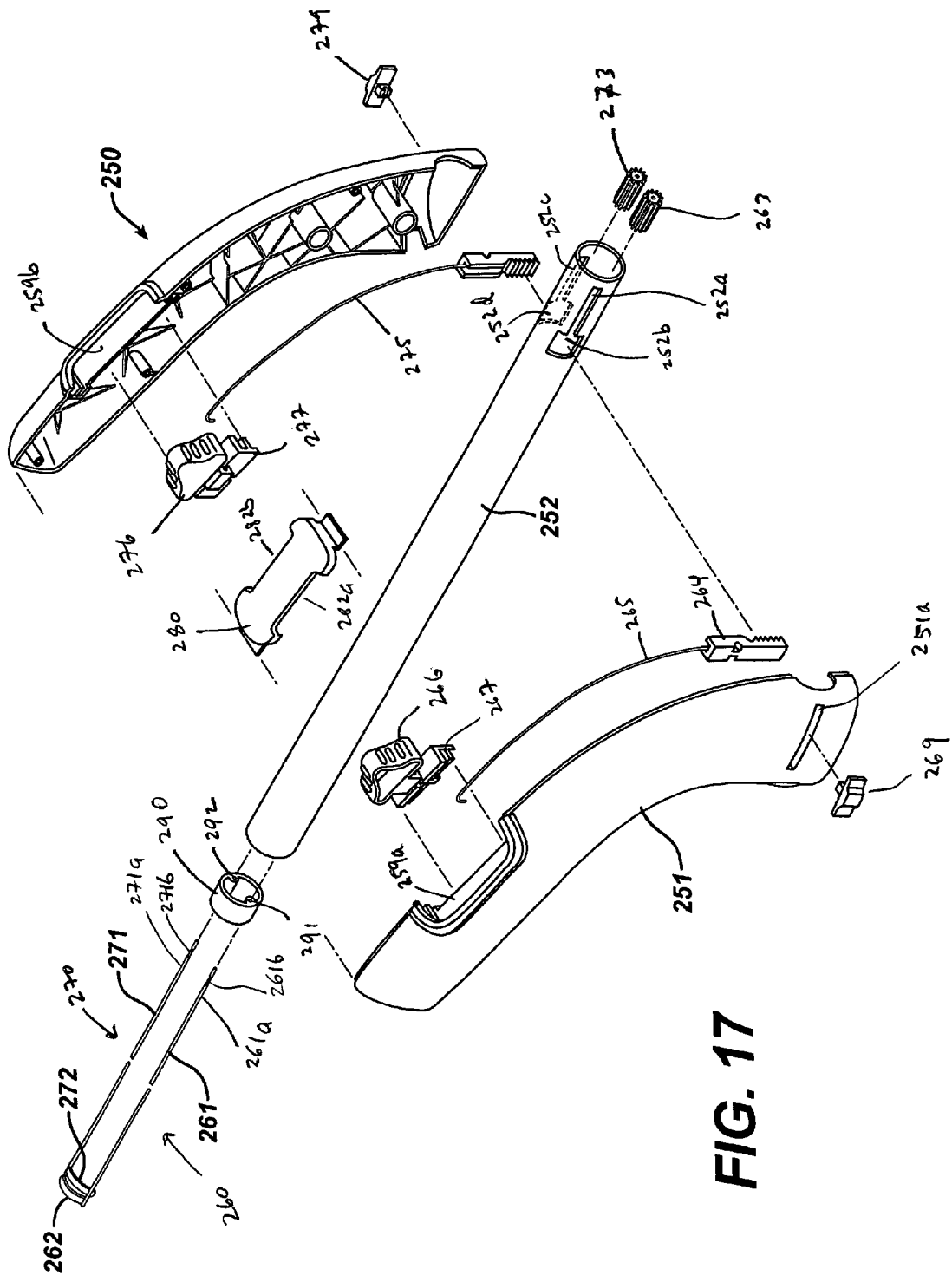
FIG. 17 is an exploded view of the retractor shown in FIG. 14.

Similar to the first embodiment, instrument 250 includes a vessel manipulator system for manipulating a vessel during EVH by repositioning the vessel within the operating field. In a preferred embodiment, instrument 250 includes a first manipulator 260 and a second manipulator 270, each disposed at least partially within cannula 252. Referring to FIG. 17 in particular, first manipulator 260 includes a first rod 261 having a first paddle 262 extending from the distal end of first rod 261. Similarly, second manipulator 270 includes a second rod 271 having a second paddle 272 extending from the distal end of second rod 271. First and second rod 261, 271 are preferably made from stainless steel wire having a diameter approximately in the range of 0.025 inch to 0.075 inches, but most preferably 0.050 inches. While first and second manipulators 260, 270 are depicted as similar to manipulators 60 and 70 of FIGS. 1-10, manipulators 160 and 170 of FIGS. 11-13 can also be used in connection with this embodiment.

Instrument 250 includes a first actuation system 268 having a first actuator 266 operably attached to first paddle 262. First actuator 266 includes a button that the user moves to generate rotation of first paddle 262. First actuator 266 preferably also includes a slide 267 either integral with or separably attached to first actuator 266. First slide 267 is configured to retain one end of a wire 265 and to slidably ride in a slot 282a formed by lip 259a of handle 251 and a spacer 280. First wire 265 is connected at a distal end to first slide 267 and at a proximal end to a first rack 264. First rack 264, in turn is matingly engaged with a first pinion 263 through window 252b of cannula 252.

The first actuation system also includes a first slide actuator 269 for moving first rod 261 axially in and out of cannula 252. Slide actuator 269 rides in slot 251a of handle 251 and slot 252a of cannula 252. Slots 251a and 252a communicate along their length. Slide actuator 269 is attached to first rod 261 at a proximal end 261a. First rod 261 is preferably snap-fitted to slide actuator 269 at a narrowed section 261b. First rod 261 is attached at proximal end 261a to first pinion 263. Pinion 263 is preferably of a length that mates with rack 264 at each of the stowed, forward and extended positions.

Continuing to refer to FIG. 17, instrument 250 includes a second actuation system 278 having a second actuator 276 operably attached to second paddle 272. Second actuator 276 includes a button that the user moves to generate rotation of second paddle 272. Second actuator 276 preferably also includes a slide 277 either integral with or separably attached to second actuator 276. Second slide 277 is configured to retain one end of a wire 275 and to slidably ride in a slot 282b formed by lip 259b of handle 251 and spacer 280. Second wire 275 is connected at a distal end to second slide 277 and at a proximal end to a second rack 274. Second rack 274, in turn, is matingly engaged with a second pinion 273 through window 252d of cannula 252. The second actuation system also includes a second slide actuator 279 for moving second rod 271 axially in and out of cannula 252. Slide actuator 279 rides in slot 251b of handle 251 and slot 252c of cannula 252. Slots 251b and 252c communicate along their length. Slide actuator 279 is attached to second rod 271 at a proximal end 271a. Second rod 271 is preferably snap-fitted to slide actuator 279 at a narrowed section 271b. Second rod 271 is attached at proximal end 271a to first pinion 273.

Cannula 252 includes a spacer 290 disposed within or formed as a part of cannula 252. Spacer 290 has throughholes 291 and 292 sized to accommodate rods 261, 271 respectively, such that rods 261, 271 are slidable within throughholes 291, 292.

Figure 14A:
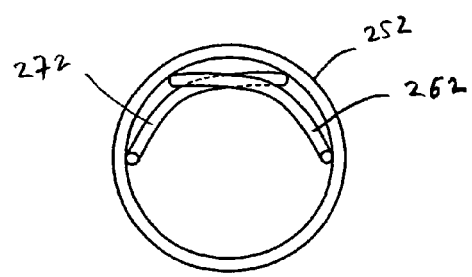
FIG. 14A is a sectional view of the retractor shown in FIG. 14 taken along line 14A-14A.

The actuation of the second embodiment is now described. Referring to FIGS. 14 and 14A, first actuator 266 and second actuator 276 are shown in their most proximal position, or the position closest to the operator's hand, within slots 282a and 282b. In this position, paddles 262 and 272 are retained within cannula 252 in their stowed position. The user positions cannula 252 within an operative space formed by an insufflation fluid passed through cannula 252 or by some other means. Alternatively, cannula 252 can include a slidable beam (not shown) that moves from a position substantially disposed within cannula 252 to a position distal to the distal end of cannula 252 to create an operative space mechanically. In this way, an insufflation fluid is not necessary.

Figure 15:
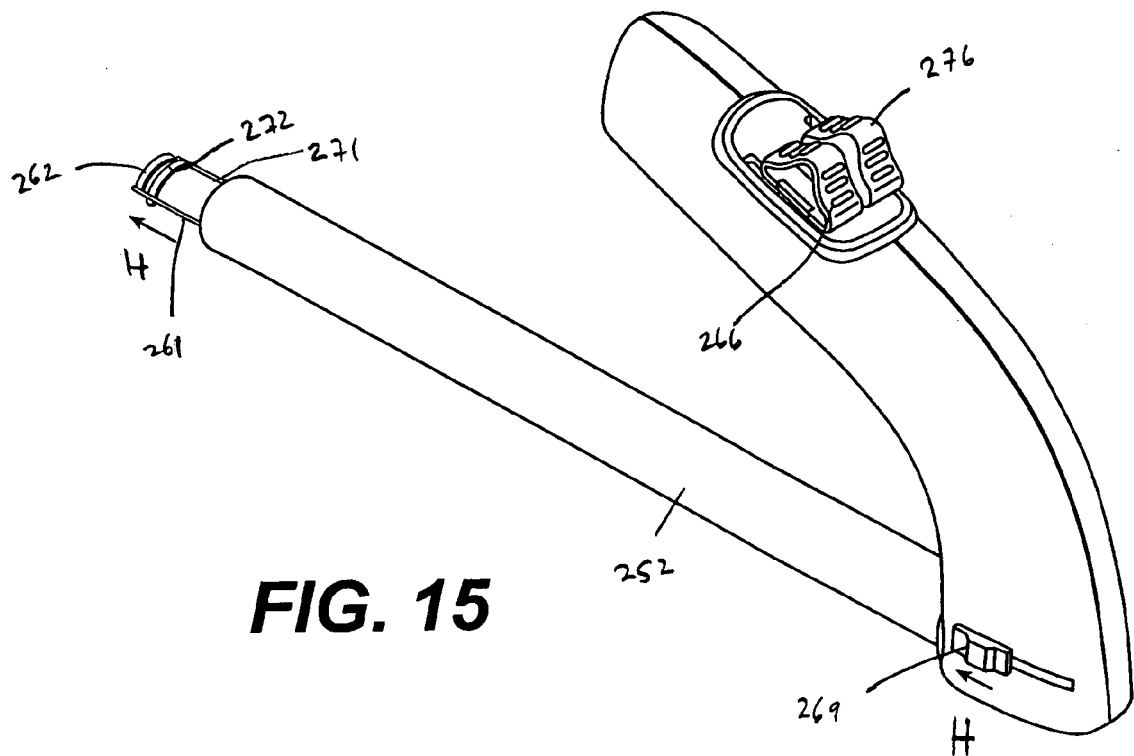
FIG. 15 is a perspective view of the retractor shown in FIG. 14 with the paddles in the forward position.
Figure 16:
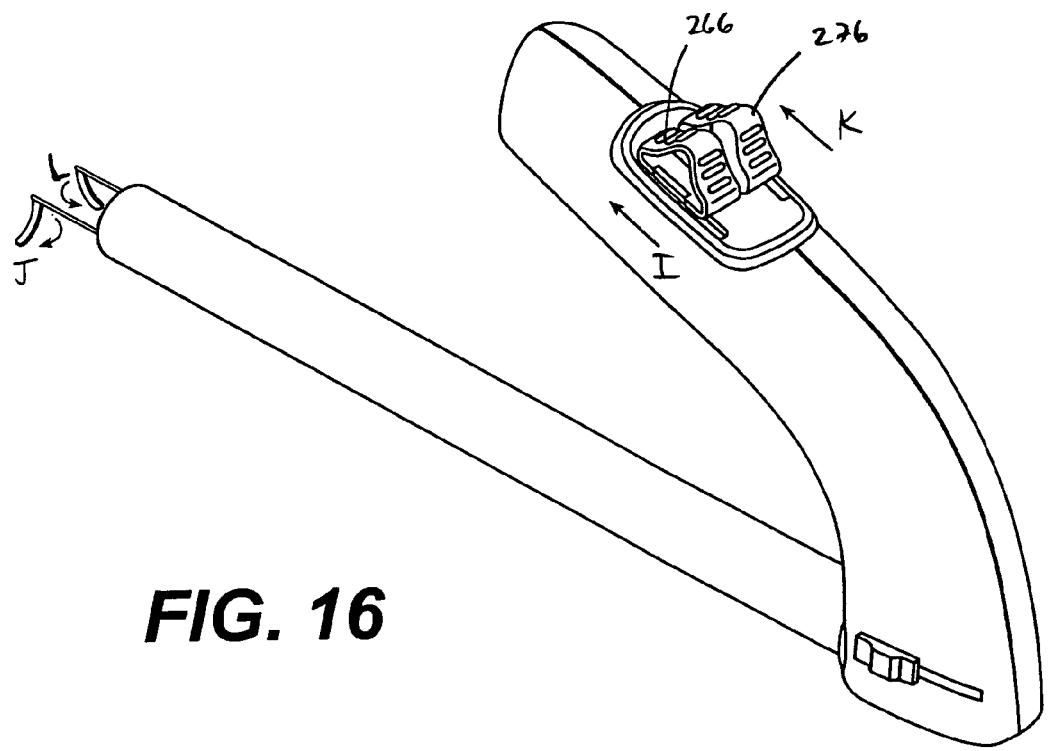
FIG. 16 is a perspective view of the retractor shown in FIG. 14 with the paddles in the extended position.

Referring to FIG. 15, displacement of first slide actuator 269 in the distal axial direction indicated by arrow H, causes first paddle 262 to be displaced a similar distance such that paddle 262 extends out the distal end of cannula 252 to the forward position. Similarly, and as is depicted in FIG. 15, when second slide actuator 279 is extended in the axial direction, second paddle 272 is also extended from the stowed position to the forward position. Referring to FIG. 16, when first actuator 266 is moved distally (or away from the operator's hand), in a direction depicted by arrow I, first wire 265 moves upwardly and distally, which in turn causes first rack 264 to move upwardly. The motion of first rack 264 in turn causes first pinion 263 to rotate in the clockwise direction depicted as arrow J. As pinion 263 is attached to rod 261, rotation of first pinion 263 causes first paddle 262 to also rotate in the clockwise direction. Similarly, moving second button 79 distally in a direction depicted by arrow K causes second wire 275 to move upwardly and distally, which in turn causes second rack 274 to move upwardly, causing second pinion 273 and second paddle 272 to rotate in a counter-clockwise direction shown by arrow L.

Figure 18:
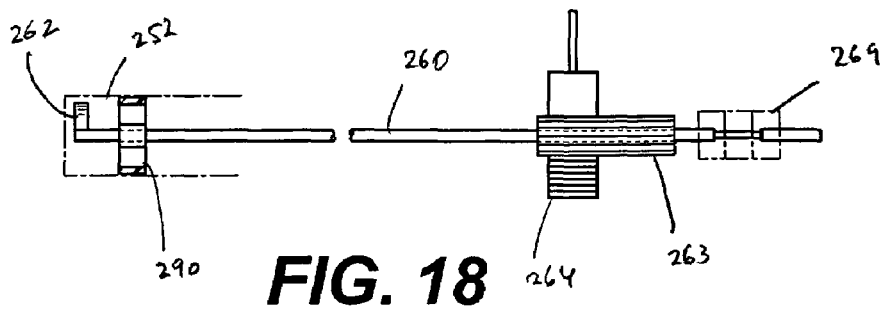
FIGS. 18-20 are graphic representations of one embodiment of the actuation mechanism for the retractor shown in FIG. 14.
Figure 19:
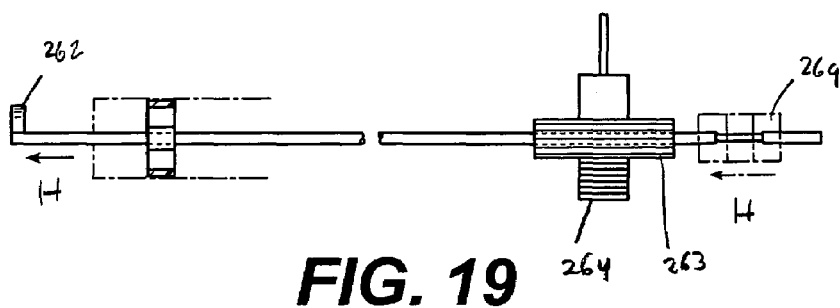
Figure 20:
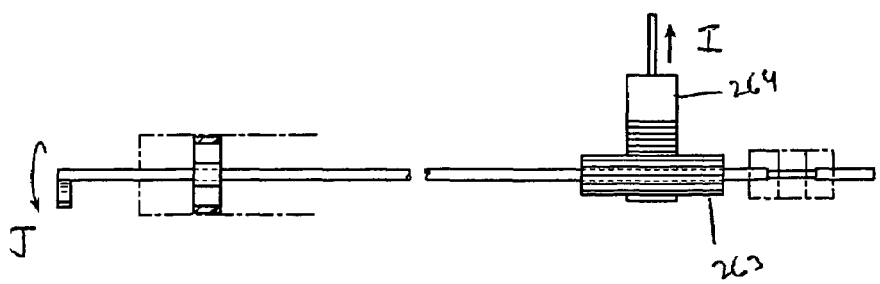

The location of first slide actuator 269 and the relative positions of rack 264 and pinion 263 are shown in FIGS. 18-20 graphically. In the stowed position, slide actuator 269 is at a proximal position and paddle 262 is disposed within cannula 252. Upon moving slide actuator axially, in a direction H, paddle 262 moves in the axial direction. Upon moving first actuator 266 in a distal direction, rack 246 is pulled in direction I, causing pinion 263 and paddle 262 to rotate in the clockwise direction J.

While the preferred embodiment depicts separate systems for providing the axial extension (slide actuator 269) and the rotation motion (first actuator 266), it is contemplated that these motions could be provided by a single actuation system that first moved axially along the length of cannula 252 for a distance long enough to permit paddle 262 to extend out of cannula 252 to the forward position, and then moved radially to rotate paddle 262. Those skilled in the art can apply the teachings here to design such a system.

While there has been shown and described what is considered to be preferred embodiments of the invention, it will, of course, be understood that various modifications and changes in form or detail could readily be made without departing from the spirit of the invention. For example, while handle 51 is depicted as an L-shaped handle, the handle could be an in-line handle, which is well-known in the art. It is therefore intended that the invention be not limited to the exact forms described and illustrated, but should be constructed to cover all modifications that may fall within the scope of the appended claims.

What is claimed is:

1. An instrument for manipulating a vessel in a patient comprising:
    a cannula having a lumen for providing insufflation to create a working space in the tissue of a patient;
    a first manipulator for manipulating a vessel located within the working space, the first manipulator slidably movable within the cannula from a stowed position, wherein the first manipulator is substantially disposed within the cannula, to a forward position, wherein at least a portion of the first manipulator is disposed outside the cannula, the first manipulator being rotatable when in the forward position to an extended position;
    a handle;
    a first actuator disposed on the handle and operably connected to the first manipulator for moving the first manipulator from the forward position to the extended position;
    a first movable rack attached to the first actuator;
    a first pinion engaged with the rack, the first pinion being connected to the proximal end of the first rod; and
    a first wire having a proximal end attached to the first actuator and a distal end attached to the first rack.

2. An instrument for manipulating a vessel in a patient comprising:
    a cannula having a lumen for providing insufflation to create a working space in the tissue of a patient;
    a first manipulator for manipulating a vessel located within the working space, the first manipulator slidably movable within the cannula from a stowed position, wherein the first manipulator is substantially disposed within the cannula, to a forward position, wherein at least a portion of the first manipulator is disposed outside the cannula, the first manipulator being rotatable when in the forward position to an extended position;
    a handle;
    a first actuator disposed on the handle and operably connected to the first manipulator for moving the first manipulator from the forward position to the extended position;
    a second actuator operably connected to the first manipulator for moving the first manipulator from the stowed position to the forward position.

3. A method of manipulating a vessel, comprising the steps of:
    Providing an instrument having a lumen for providing and insufflation fluid, and a first manipulator having a forward position and an extended position;
    Making an incision in a patient;
    Inserting at least the distal end of the instrument into the incision;
    Creating a working space in the tissue of the patient near the vessel with the distal end of the instrument by permitting an insuffiation fluid to flow through the lumen and into the incision; and
    manipulating the vessel by rotating the first manipulator from the forward position to the extended position.

4. The method of claim 3, wherein the first manipulator is disposed at least partially within the instrument in stowed position, and comprising the step of moving the first manipulator distally from the stowed position to the forward position prior to the manipulation step.

5. The method of claim 3, wherein the first manipulator comprises a first rod and a first paddle attached to a distal portion of the first rod, and the manipulation step comprises rotating the paddle about an axis defined by the first rod to move the vessel away form the distal end of the instrument.

6. A method for creating operative space and manipulating a vessel, comprising the steps of:

providing an instrument having a lumen for providing an insufflating fluid, a first manipulator and a second manipulator, the first and the second manipulators each having a forward position and an extended position;

making an incision in a patient;

inserting at least the distal end of the instrument into the incision;

creating a working space in the tissue of the patient near the vessel with the distal end of the instrument by permitting an insufflation fluid to flow through the lumen and into the incision; and manipulating the vessel by moving one of the first manipulator and the second manipulator from the forward position to the extended position.

* * * * *